(12) United States Patent
Jahoda et al.

(10) Patent No.: US 7,419,661 B2
(45) Date of Patent: Sep. 2, 2008

(54) DERMAL SHEATH TISSUE IN WOUND HEALING

(75) Inventors: Amanda Jane Jahoda, Durham (GB);
Colin Albert Buchanan Jahoda, Durham (GB)

(73) Assignee: The Centre of Excellence for Life Sciences Limited, Newscastle upon Tyne (GB)

( * ) Notice: Subject to any disclaimer, the term of this patent is extended or adjusted under 35 U.S.C. 154(b) by 248 days.

(21) Appl. No.: 10/395,776

(22) Filed: Mar. 24, 2003

(65) Prior Publication Data

US 2004/0057937 A1 Mar. 25, 2004

Related U.S. Application Data

(62) Division of application No. 09/423,154, filed on Oct. 29, 1999, now abandoned.

(51) Int. Cl.
*C12N 5/00* (2006.01)

(52) U.S. Cl. .................. 424/93.7; 424/93.1; 424/422

(58) Field of Classification Search .............. 424/93.7
See application file for complete search history.

(56) References Cited

U.S. PATENT DOCUMENTS 4,919,664 A * 4/1990 Oliver et al. ............... 128/898

FOREIGN PATENT DOCUMENTS

| EP | 0236 014 | 9/1987 |
|---|---|---|
| EP | 0285 471 | 10/1988 |
| EP | 0405 656 | 1/1991 |
| WO | WO 83 01384 | 4/1983 |
| WO | WO 93 25660 | 12/1993 |
| WO | WO 95 01423 | 1/1995 |
| WO | WO 97 25995 | 7/1997 |

OTHER PUBLICATIONS

Kim et al., Dermatologic Surgery 21(4): 312-313 (Apr. 1995). Abstract.*
Jahoda et al., J. Cell Sci. 99: 627-636 (1991). Abstract.*
Jahoda et al., Development 114: 887-897 (1992). Abstract.*
Home et al., Development 116: 563-571 (1992).*
Prouty et al., 1996, Am J Pathol, 148:1871-85.
Scandurro et al., 1995, J Invest Dermatol, 105:177-83.

* cited by examiner

*Primary Examiner*—L Blaine Lankford
*Assistant Examiner*—Allison M. Ford
(74) *Attorney, Agent, or Firm*—Klauber & Jackson LLP

(57) ABSTRACT

The invention concerns the use of dermal sheath tissue and/or cells derived therefrom in wound healing systems. Specifically, the relevant features of this tissue type have been exploited to provide a novel wound healing material that has application in the provision of new therapeutic compositions and new surgical dressings where wound closure and minimal scarring is desirable.

13 Claims, 10 Drawing Sheets

DERMAL SHEATH TISSUE IN WOUND HEALING

RELATED APPLICATION

The present application is a Division of application Ser. No. 09/423,154, filed Oct. 29, 1999, now abandoned the entire disclosure of which is incorporated herein by reference. Applicants claim the benefit thereof under 35 U.S.C. §120.

The invention relates to the use of dermal sheath tissue and/or cells derived therefrom and/or portions of hair follicles containing these and other cell populations for use particularly, but not exclusively in wound healing and/or skin models.

Skin is a highly complex organ covering the external surface of the body and merging, at various body openings, with the mucous membranes of the alimentary and other canals. It has multiple functions such as preventing water loss from the body, but predominantly acts as a protective barrier against the action of physical, chemical and bacterial agents on deeper tissues. Skin is elastic and except for a few areas such as the palms, soles and ears it is loosely attached to underlying tissue. It varies in thickness from 0.5 mm (0.02 inches) on the eyelids to 4 mm (0.17 inches) or more on the palms and soles.

Skin is composed of two layers (please refer to FIG. 1 which illustrates an anatomical cross-sectional view through a slice of skin), the outer layer, which is comparatively thin (0.1 mm) is called the epidermis, or cuticle, it is several cells thick and has an external, horny layer of dead cells that are constantly shed from the surface and replaced from below by a basal layer of cells, called the stratum germinativum. The epidermis is composed predominantly of keratinocytes which make up over 95% of the cell population, the rest include dendritic cells such as Langerhans cells and melanocytes. It is essentially cellular and non-vascular, there being relatively little extracellular matrix except for the layer of collagen and other proteins beneath the basal layer of keratinocytes. Keratinocytes of the basal layer are constantly dividing, and daughter cells subsequently move outwards, where they undergo a period of differentiation and are eventually sloughed off from the surface. The inner layer of the skin is called the dermis and is composed of a network of collagenous extracellular material, elastic fibres, blood vessels and nerves. Contained within it are hair follicles with associated sebaceous glands (collectively known as the pilosebaceous unit) and sweat glands. The interface between the epidermis and dermis is extremely irregular and consists of a succession of papillae, or finger like projections. Beneath the basal epidermal cells along this interface the specialised extracellular matrix is organised into a distinct structure called the basement membrane.

The mammalian hair fibre is the product of a small peg of tissue known as the hair follicle which lies immediately underneath the skin's surface. The distal part of said follicle is in direct continuation with the cutaneous epidermis externally. Although small, the follicle comprises a highly organised system of recognisably different layers arranged in concentric series. Active hair follicles extend down through the dermis, the hypodermis (a loose layer of connective tissue), and the fat or adipose layer.

At the base of any active follicle lies the hair bulb, which consists of a body of dermal cells, known as the dermal papilla, contained in an inverted cup of epidermal cells known as the epidermal matrix (please refer to FIG. 1). Irrespective of follicle type, the hair fibre, together with several supportive epidermal layers, is produced by germinative epidermal cells at the very base of this epidermal matrix. The lowermost dermal sheath is contiguous with the papilla basal stalk, from where it curves externally around all of the epidermal layers of hair matrix as a thin covering of tissue, and then continues as a tube or sleeve for the length of the follicle. The dermal sheath is otherwise known as the connective tissue sheath.

Developing skin appendages such as feather and hair follicles rely on interaction between the skin's two layers, the epidermis and the dermis. In embryonic development, a sequential exchange of information between these layers underpins a complex series of morphogenetic processes culminating in the formation of adult follicle structures. However, following maturity, and in contrast to general skin dermal and epidermal cells, certain hair follicle cell populations retain embryonic-type inductive, interactive and biosynthetic behaviours. These properties are likely to derive from the very dynamic nature of the cyclically productive follicle, in which repeated tissue remodelling necessitates a high level of dermal-epidermal interactive communication, as is vital for embryonic development and, as would be desirable in any form of tissue reconstruction.

Hair fibre is produced at the base of an active follicle at a very rapid rate (0.4 mm per day in the human scalp follicles and up to 1.5 mm per day in the rat vibrissa or whiskers), which means that cell proliferation in the follicle epidermis ranks amongst the fastest in adult tissues (1).

The most dynamic region of the hair follicle is the deeply embedded end bulb, where local dermal-epidermal interactions drive active fibre growth. This same region is also central to the developmental changes and tissue remodelling involved in the hair fibre's or appendages precise alternation between growth and regression phases. As a key player in the activities, the dermal papilla appears to orchestrate the complex program of differentiation that characterises hair fibre formation from the primitive germinative epidermal cell source (2-5). The lowermost dermal sheath initiates below the papilla basal stalk, from where it curves outwards and upwards to externally enclose all of the layers of the epidermal hair matrix as a thin cup of tissue. (Please refer to FIG. 1). The dermal sheath continues as a tubular arrangement for the length of the follicle, as does the epidermal outer root sheath which lies immediately internal to it in between the two layers is a specialised basement membrane termed the glassy membrane. The outer root sheath constitutes little more than an epidermal monolayer in the lower follicle, but becomes increasingly thickened more superficially.

Pioneering studies established that rat whisker follicles whose end bulbs had been amputated, could regenerate all of the crucial elements that were required to restore fibre growth (6). They also revealed that the isolated dermal papilla had particularly powerful interactive capabilities in being able to induce completely new hair follicles when re-implanted in vivo (2). Subsequent experiments gave further support to what had been found in rats (4, 7-9), and confirmed that papillae from other species, including mice (10, 11) and sheep (12) had similar interactive capabilities. Human facial (13) and axillary (14) follicles in situ, as well as, isolated human follicles transplanted to rodent hosts (15), have also been reported to regenerate following amputation. Further studies in vitro strongly suggested that human follicle tissues and cells displayed the highly specialised interactive properties that were seen in their rodent counterparts (16).

Whilst the individual anatomical components and cell subpopulations of skin are well established their intra/inter biochemical interactions and control mechanism remains largely a matter for speculation and intense research.

Destruction of extensive areas of skin is caused by injury, burns, disease or large ulcers. Regeneration of skin over denuded areas takes place naturally by cell proliferation from the surrounding margins of healthy undamaged skin and the underlying skin appendages when these remain. A specific clinical problem that occurs naturally as a result of wound healing is hypertrophic scarring, where the balance between new collagen production and collagen breakdown is not in equilibrium, and there is an overproduction of scar tissue which can inhibit coverage of the wound with new epidermis. This is quite common, but it usually subsides. However in some cases the condition can worsen and keloid scars (masses of extracellular matrix that keep on growing) can be produced. Clinically this can be treated by steroids if minor, but more serious cases are extremely difficult to treat and often result in surgery. However, if the area of denuded/damaged skin is large and of full thickness then complete coverage of the damaged area is facilitated by the use of skin grafts, sections of skin of either full or partial thickness are removed from a remote part of the body (donor site) and applied to the raw surface (recipient site).

It should be noted that generally grafts are taken from skin transplanted from the body of the same individual (autographs). In a successful transplant the graft is nourished at first by the serum oozing from the damaged area and subsequently by capillary invasion from underlying tissue into the graft.

Graft survival has long been acknowledged to be affected by its immunogenicity in relation to the site it is transplanted to. As an extreme example, females are very intolerant of male tissue—largely due to their reaction against male-specific (H-Y) antigens (17). The skin is well known for its notoriously poor support or tolerance in this context (18, 19).

Over the years a multitude of approaches have been followed in an attempt to create a viable model with which to study cutaneous physiology and morphology, and/or which can be used for medical grafting procedures.

There are four or more common types of dermal support in skin wound models:
a) native collagen (dermis treated to remove cellular elements which subsequently becomes re-cellularised);
b) collagenous gels or lattices (made from extracted collagen which is then reconstituted) and,
c) highly complex mixtures of reconstructed collagen and a multitude of extracellular matrix products (from sources as diverse as mouse tumours and shark fins).
d) neonatal or young donor skin fibroblasts (thus less immunogenic) grown on a biomatrix, and allowed to attach and produce their own extracellular matrix. This is then transplanted in either the cellular form as a "living skin" or cell free, using the extracellular matrix that has been produced by the cells.

All of these methodologies incorporate the use of ordinary skin fibroblasts, and none produce models or substitutes that are truly representative of normal skin structure. Moreover, they are often very time consuming and extremely expensive to prepare.

Wound healing or contracture can be a painful process both physiologically and psychologically. Scarring can lead to disfiguration and deformation, in some cases the taughtness and/or adhesions, as a result of scar tissue formations, can cause damage to surrounding and/or underlying tissue and/or loss of regional elasticity and/or sensation. In humans, much of the problem associated with full thickness wounds/burns/injury/trauma is that a normal thickness dermis is not restored, which can result in depressions and/or indentations in the scar region. Many animals have a "looser" skin than humans and have a greater capacity for contraction, as exemplified by removal of a large 2 cm full thickness patch of skin from a rabbit back and reduction of the site to a scar, that is a barely visible line, in a matter of two weeks. Consequently aiding/enhancing contraction could reduce the size of scarred region. Furthermore, it is our belief that the known phenomenon of rapid human scalp wound healing, compared to wound healing rates in other parts of the body which have lower follicle density, or with fewer large active follicles, is due to the abundance of available dermal sheath cells which, as myofibroblasts, assist in wound contraction. This idea is against the prevailing wisdom, in which the rapid healing properties of the scalp skin are attributed to greater vasculature in this region.

Wound contracture is a very important part of the process by which skin heals, and it is thought that a transient population of cells called myofibroblast, effect this closing of the damaged site by contraction. The exact source of the myofibroblast has not been identified, but said cells are characterised by their expression of alpha smooth muscle actin. An invention to improve wound healing would have immediate benefit and wide application since it is estimated that over 2 million people suffer serious burns in the US alone each year, and many of those require grafts.

Several experimental approaches to artificial skin grafts have been tried, for example epithelial sheets have been grown in culture from interfollicular skin and grafted back onto the donor at a later date—but although life-preserving, this method is often unsatisfactory because the sheets are delicate and difficult to transfer. Also, since there is no supportive dermis involved, dermal indentations are left at the graft site because a normal full thickness dermis is not restored. Their simplicity leaves them unrepresentative of a skin model for studies in vitro, while in relation to grafting, at best, they merely act as covers while the patients own skin can recover.

Alternative approaches have been attempted employing skin basal and outer root sheath epidermal cells have been cultured on collagen gels (with or without skin fibroblasts), or other natural or synthetic dermal substitutes, with the same ultimate objective, but again may of these approaches have specific limitations, usually related to survival or inability to resemble normal skin. Of the prior art approaches it is claimed that outer root epidermal sheath cells in combination with a dermal component provide the best results on wound patients. Thus, in spite of demand and the provision of complex supportive biochemical constituents, the current in vitro skin models are deficient in that:
1) their epidermal component does not undergo normal differentiation;
2) they do not develop the skin's normal biosynthetic dermal-epidermal barrier (a kind of biological filter and message processor) called the basement membrane;
3) they lack constituents such as hair follicles and sweat glands;
4) they are fragile, difficult to handle and cannot be maintained;
5) they cannot avoid disfigurement because they cannot fill tissue void;
6) they do not prevent infection or restore living/effective tissue so inflexible non-functional scars can develop.

Therefore in terms of faithful in vitro systems, and as material for skin replacement, present models/substitutes are deficient.

Recent papers in the area emphasise the desperate need for more research to try and find a suitable backing material for epidermal grafts that will promote a high level of 'take'. We propose that the prior art failures are largely due to the lack of a favourable wound bed dermis for epidermal cells to attach to, when the full thickness of skin has been lost—we believe that the dermal sheath cells are the natural candidates for this role, and that successful tissue engineering can only occur when the appropriate cells for the job are employed.

The most important of all cells types are those at the source of every biological system ie stem cells, since they vitally sustain and replenish the more differentiated descendent population and as they become specialised develop a characteristic function. Yet these are the cells which are least understood in terms of their distribution, behaviour and the factors by which they may be defined. The ability to provide significant numbers of pure, unstimulated, undifferentiated, primitive stem cells from an adult organ would be likely to have a broad impact on our fundamental understanding of cell biology, and would yield positive and promising approaches to future therapeutic advances.

Serendipitously, we have studied hair follicles and identified a specific cell population with immune privilege and stem specific cell potential that can be used in a most advantageous way to aid and enhance wound healing.

We have found that simple forms of follicle cell(s) provide dermal-epidermal recombination (under very basic culture conditions) resulting in previously undocumented basement membrane formation and appendage-specific epidermal differentiation, and that these follicle cells can readily exhibit certain major characteristics that to date have been missing from skin model systems. Further natural attributes that predispose follicle cells as candidates for the applications of wound healing include their: similarity to wound myofibroblasts; exhibition of stem cell-type qualities; production of a unique embryonic-type extracellular matrix and, the fact that they exhibit impressive regenerative and inductive abilities.

Thus, in at least three key areas (basement membrane formation, normal epidermal differentiation over a naturally supportive dermis and the incorporation of skin appendages) we are able to deliver immediate improvements to the currently available skin graft alternatives and in vitro skin models. Hence, by utilising a specific and isolated tissue or cell type ie dermal sheath tissue and/or cells derived therefrom and incorporating them in a reconstructed graft or graft composite, we are able to produce a more appropriate skin substitute which overcomes many of the problems associated with the prior art.

It is therefore an object of the invention to provide a new wound healing system that employs self derived cells/tissues and/or their attributes.

It is a yet further object of the invention to provide a wound healing system that employs non-self derived cells tissues and/or their attributes.

It is a yet further object of the invention to provide a wound healing system of multi-potential use ie for use in acute and/or chronic and/or minor and/or severe wound healing situations.

According to a first aspect of the invention there is provided dermal sheath tissue and/or cells derived therefrom for use in a wound healing system.

In a preferred embodiment of the invention said dermal sheath tissue and/or said cells is/are derived from a selected portion of a follicle ideally the lower third thereof and even more ideally are derived from an ring of cells about or around said follicle, ideally an inner ring, and most ideally said tissue/cells is/are positive for smooth muscle actin.

In a preferred embodiment of the invention said tissue and said cells derived therefrom are provided or combined with at least one other cell type from a hair follicle, and most ideally are combined with tissue comprising the dermal papilla, or cells derived therefrom. This combination is favoured because our experiments have shown that dermal papilla tissue, or cells derived therefrom may assist in the closure of wound and in the reduction of scar tissue.

In a yet preferred embodiment of the invention there is provided a wound healing system comprising a suitable matrix material having incorporated and/or embedded therein and/or associated therewith and/or attached thereto dermal sheath tissue and/or cells derived therefrom. Ideally said matrix material comprises native collagen or collagenous gels or lattices constructed from reconstituted collagen or highly complex mixtures of reconstituted collagen and a multitude of extracellular matrix products or any other suitable matrix material known to those skilled in the art, the selection of which is not intended to limit the scope of the invention.

In a yet further preferred embodiment of the invention there is provided a surgical dressing comprising a web material and a suitable matrix material, at least one of which materials has incorporated and/or embedded therein and/or associated therewith and/or attached thereto dermal sheath tissue and/or cells derived therefrom. Ideally said surgical dressing is conventional, the selection of which is not intended to limit the scope of the invention.

In a yet further preferred embodiment of the invention there is provided a therapeutic composition comprising a suitable carrier for dermal sheath tissue and/or cells derived therefrom, ideally said carrier can be formulated to have anti-bacterial properties and/or anti-septic properties and more ideally further include growth promoting additives and/or local anaesthetics. Ideally said therapeutic composition may be adapted to be applied topically in the form of dermal sheath cells suspended in a suitable carrier solution/gel/cream/emollient; alternatively said composition may be adapted to be administered by injection and so comprise a carrier solution; alternatively still, said carrier may be incorporated and/or embedded therein and/or associated therewith and/or attached thereto a plaster or bandage or the like.

In a yet further preferred embodiment of the invention there is provided a suitable matrix material having incorporated and/or embedded therein and/or associated therewith and/or attached thereto dermal sheath tissue and/or cells derived therefrom for implantation.

According to a second aspect of the invention there is provided dermal sheath tissue and/or cells derived therefrom for use in a reconstructed graft for use in the treatment of skin injury where dermal replacement is required.

In yet a preferred embodiment of the invention said tissue and/or cells are further provided or combined with at least one other cell type, said cell type being derived from a hair follicle and ideally comprising dermal papilla tissue and/or cells derived therefrom.

In a yet further preferred embodiment of the invention there is provided dermal sheath tissue and/or cells derived therefrom for use in in vitro modelling, ideally, and optionally, in combination with at least one other cell population derived from skin.

According to a third aspect of the invention there is provided a wound healing system as hereinbefore described for use in treatment of acute and/or chronic and/or minor and/or severe wound healing; and/or cartilage repair and/or bone repair and/or muscle repair and/or connective tissue repair and/or blood vessel repair.

According to a fourth aspect of the invention there is provided dermal sheath tissue and/or cells adapted so as to provide a protective layer of cells/capsule wherein said layer of cells/capsule is suitably positioned on or about an organ that is to be allografted to a patient/recipient. In this aspect of the invention the immunoprotective quality of the dermal sheath tissue and/or cells derived therefrom is exploited.

In any of the above aspects of the invention said dermal sheath tissue may be derived from self or more preferably from non-self.

In summary, we believe the dermal sheath tissue and/or cells derived therefrom have an important part to play in wound healing and/or wound modelling because this tissue and/or cells derived therefrom has been shown to participate in wound contraction, wound dermis replacement-including the replacement of a variety of dermis types depending upon the site of the wound, increasing wound strength and status, supporting epidermal growth, a reduction in scarring-indeed this tissue type, and/or in combination with dermal papilla cells can lead to scarless wound healing, and moreover, this tissue type can be stored long term at low temperatures and still retain the aforementioned properties, thus wound healing therapeutics and wound cell models can be reliably manufactured and then stored for future use. Additionally, this tissue and/or cells derived therefrom can exist for a long time in culture under extreme stress, thus wound healing therapeutics and/or wound cell models of this sort are robust in nature, another favourable advantage in terms of storage, and subsequent application.

An embodiment of the invention will now be described by way of example only with reference to the following Figures wherein:

as shown in FIG. 2e, marked by a star (*).

FIG. 12 represents pictorial evidence of dermal sheath cell capability to differentiate into different mesenchymal cells.
(A) Long term cultured (over a year) human dermal sheath cells.
(B) Dermal sheath cells appearing to fuse in myoblast (muscle-like) fashion.
(C) Myotube-like structures in dermal sheath cell cultures.
(D) Adipocyte (fat producing) cells.
(E) Chondrocyte (cartilage-type) cells.
(F) Mineral producing bone precursor cells—Von Kossa stained.
(G) Dermal sheath cells labelled immunohistochemically for alpha-smooth muscle actin.
(H) Human dermal sheath cells positively stained for smooth muscle myosin.
(I) Dermal sheath cells labelled positively for desmin.

Figure 13:
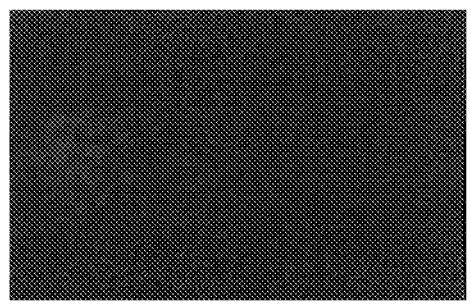

FIG. 13 represents pictorial evidence of skin at the margin of a wound and in which dermal sheath cells have surrounded an isolated follicle in the undamaged tissue away from the main group of labelled cells remote in undamaged tissue.

EXPERIMENTAL APPROACH

Tissue Isolation

Figure 1:
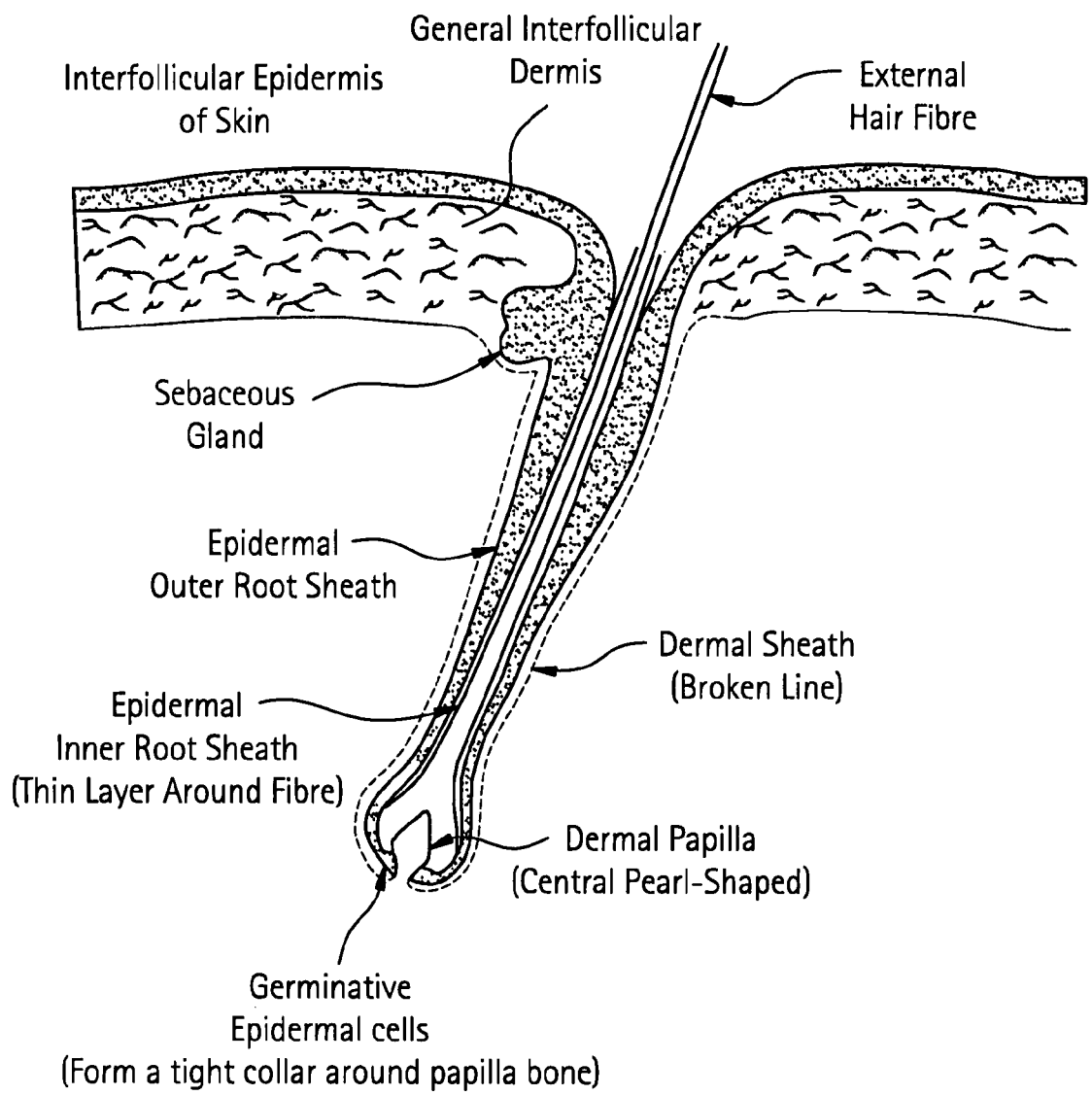
FIG. 1 represents a diagrammatic illustration of an anatomical cross-sectional view through a slide of skin.
Figure 2:
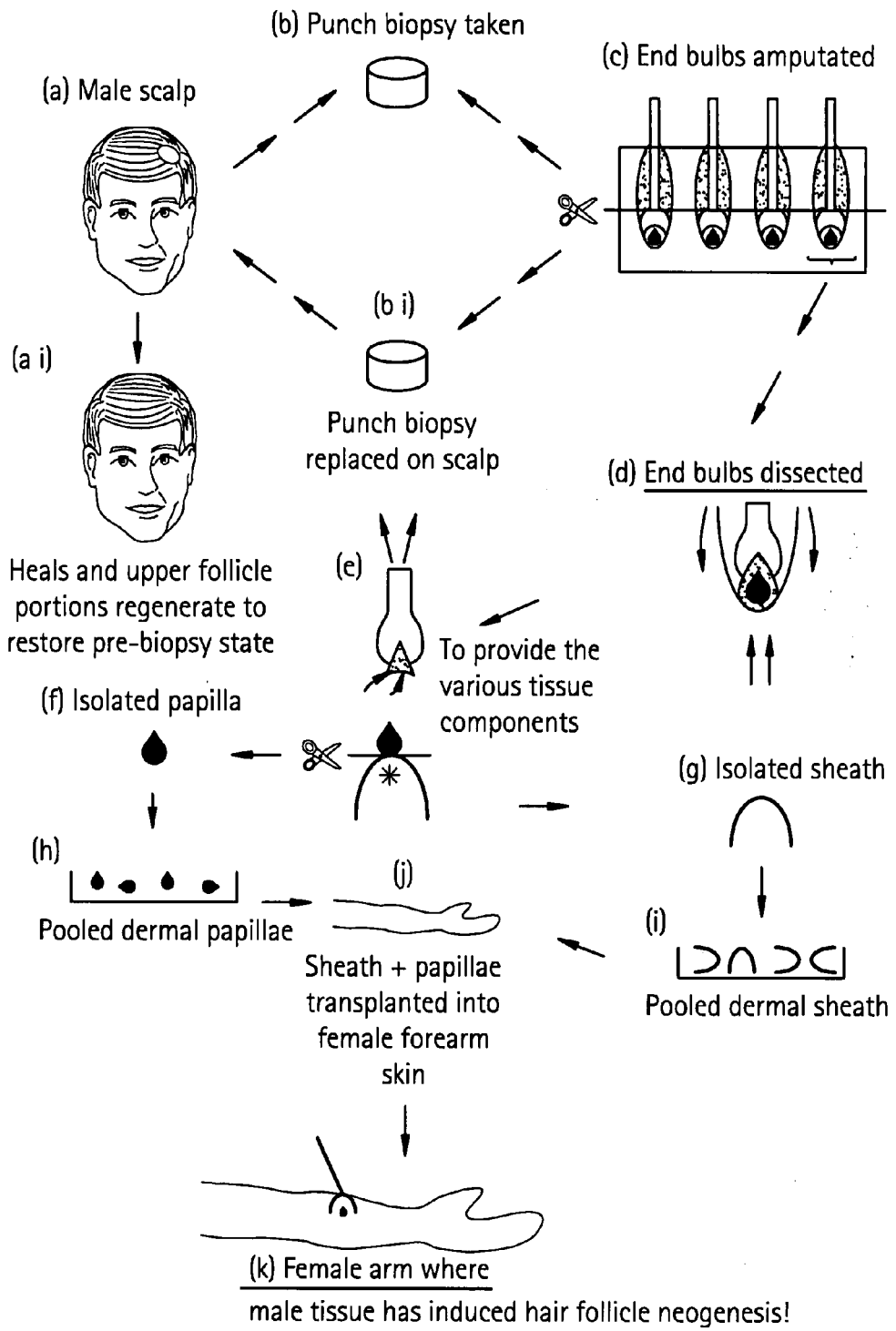
FIG. 2 represents a diagrammatic representation of procedures.
Figure 3:
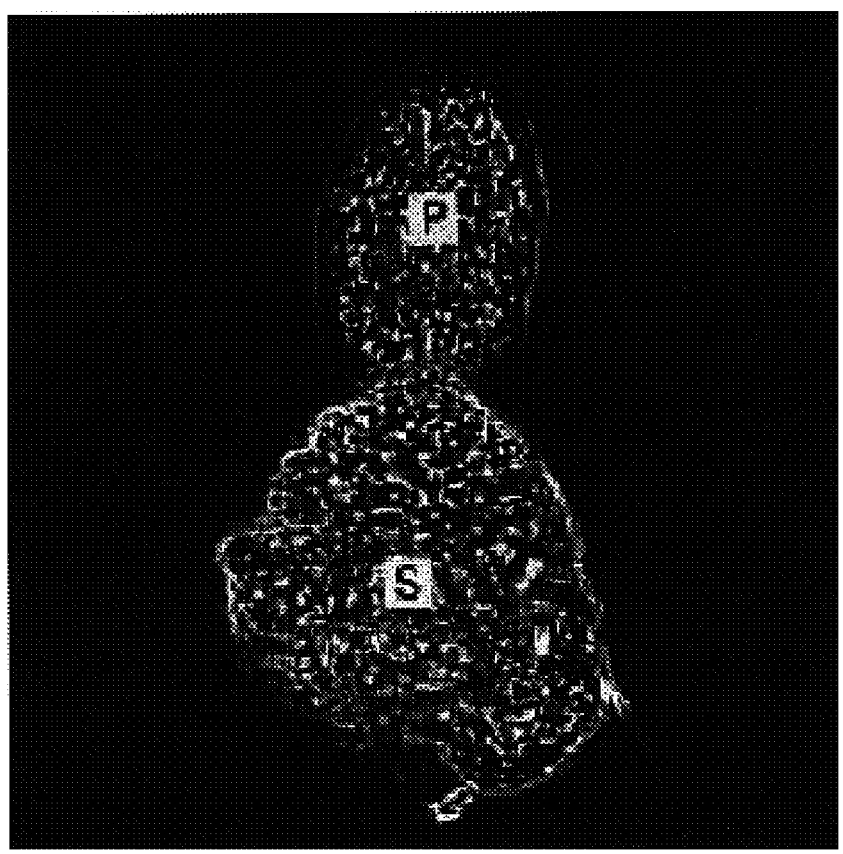
FIG. 3 represents pictorial evidence of isolated dermal papilla (P) and sheath (S) tissue microdissected from male scalp hair follicle end bulbs.

A small patch of male scalp skin (about 1.5 $cm^2$) was coarsely shaven, leaving some fibre still exposed to allow for subsequent plucking. The area was wiped with an antiseptic solution and injected locally with lignocaine plus adrenaline anaesthesia, before taking a 6 mm diameter punch biopsy at an angle appropriate to follicle orientation. The most proximal tips (under ⅕th of length) of the exposed follicles were amputated under a dissecting microscope (Zeiss) from the inverted biopsy, and transferred to individual drops of minimal essential medium (Gibco) at 4° C. After plucking the hair fibres from the transected follicles, the biopsy was returned to its original scalp skin site and left to heal. This initial procedure lasted about 20-25 mins. Refer to FIG. 2 (a, a1, b, b1 and c) which represents a diagrammatic representation of procedures. The outermost end bulb dermal layers were inverted to allow the epidermal matrix (including undifferentiated tissue) to be scraped away and discarded (FIG. 2d). Dermal papillae, isolated by basal stalk severance (FIG. 2e), were pooled in fresh medium (FIG. 2h). The thin external covering of connective tissue was then teased from the pieces of sheath dermis before they were similarly pooled in fresh medium. (FIGS. 2g and i). FIG. 3 represents pictorial evidence of isolated dermal papilla (P) and sheath (S) tissue microdissected from male scalp hair follicle end bulbs as shown in FIG. 2e marked by a star (*).

Implantations

These operations were so minimally invasive as to be practically imperceivable, hence, no form of local anaesthetic pretreatment was deemed necessary. This also avoided the possibility that the anaesthetic might adversely affect the tiny quantities of vulnerable dermis that were to be implanted.

A small, shallow wound was made in the inner forearm of the female recipient with the point of a scalpel blade, and; widened slightly using the tips of very fine (No. 5) watchmakers forceps (FIG. 2j). In the few instances when a tiny amount of blood or fluid was exuded, it was absorbed using tiny sterile cotton wool balls. Two sets of operations were performed.

Figure 4:
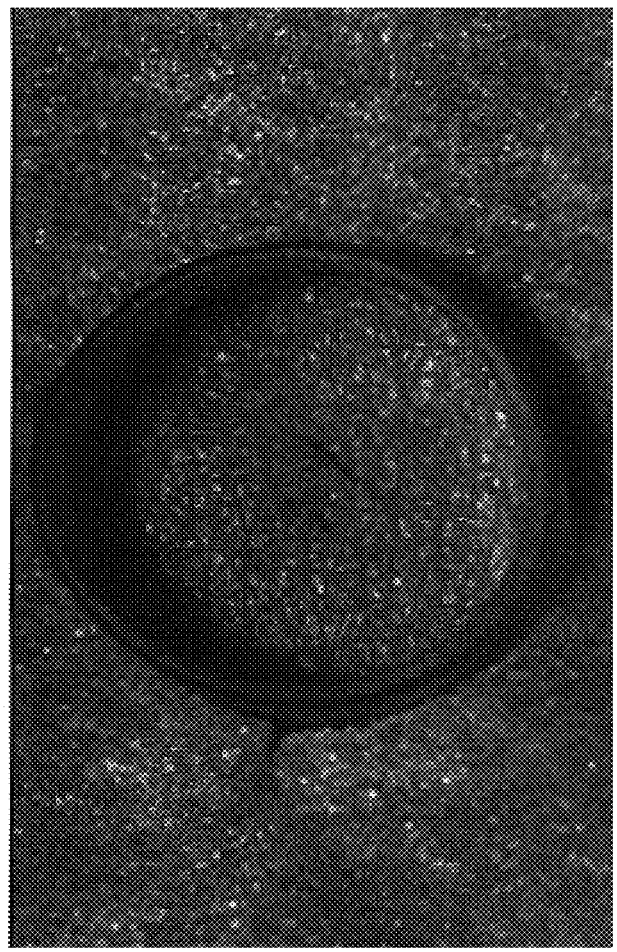
FIG. 4 represents pictorial evidence of two hair fibres which have, been produced in the immediate vicinity of the male dermal sheath-implanted female skin wound protected by a small silicone rubber collar.
Figure 5:
FIG. 5 represents pictorial evidence of FIG. 4 after the silicone collar (and plaster attachment) has been removed.

In the first, dermal sheath tissue from twelve follicles were implanted into two wound sites (six in each), approximately 10 hours after the end bulbs had been removed from the biopsy. The second, involved the implantation of 11 pieces of dermal sheath into one wound site, 9 dermal papillae into a second, and 2 papillae (which stuck to the forceps and had to be re-implanted separately) into a third, about 20 hours after biopsy. In all cases, the material was collected in as little fluid as possible and then transferred directly to the wound site, so that it could be rapidly inserted into the skin on the end of the forceps. The wounds were initially left untreated and uncovered. When hair fibres were seen emerging from the implanted sites (3-4 weeks later), small silicone rings with rims were placed over them and secured using surgical tape—as a cautionary measure to protect against abrasion, please refer to FIG. 4 which represents pictorial evidence of two hair fibres which have been produced in the immediate vicinity of the male dermal sheath-implanted female skin wound protected by a small silicone rubber collar and FIG. 5 which represents pictorial evidence of FIG. 4 after the silicon collar (and plaster attachment) have been removed.

The first set of two wound sites were biopsied together as a single piece of elliptical skin, 77 days after sheath tissue implantation, and were fixed immediately in freshly prepared 4% paraformaldehyde at pH 7.3. The second set of wounds (made 3 months after the first) were treated similarly—being removed 42 days post-operatively as two small (4 mm) punch biopsies (more precisely located by their positioning next to moles). Detailed external observations and photographic recordings of the male donor scalp, and recipient female arm skin sites, were made at regular intervals.

Fluorophore-Labelled Y-Chromosome Probe [Imagenetics]

The spectrum green fluorophore-labelled enumerator probe (Imagenetics), consisted of chromosome-specific sequences from highly repeated human satellite DNAs. The target DNA in the tissue sections was denatured in 70% formamide/2×SSC at 70° C. for 10 mins. Meanwhile, the probe mixture was prepared to contain: 7 ul SpectrumCEP hybridisation buffer (dextran sulphate, formamide, SSC, pH 7.0), 1 ul SpectrumCEP probe (fluorophore-labelled enumerator probe and blocking DNA in Tris-EDTA buffer) and 2 ul of 5× blocking solution (as detailed above), were centrifuged (1-3 secs), heated for 5 mins in a 75° C. water bath and then placed on ice. The denatured slides were washed in 70%, 85% and 100% ethanol (1 min in each) and then air dried. Each slide, heated to 45° C., received 10 ul of probe mix and then a silanised coverslip which was sealed at the edges prior to the slides incubation in a humid box at 42° C. for 18 hours. Following hybridisation and coverslip removal, the slides were washed for: 3×10 mins in 50% formamide/2×SSC; 10 mins in 2×SSC, and 5 mins in 2×SSC/0.1% NP-40, all containing Denhardts solution, 50 ug/ml sonicated salmon sperm DNA, 1% milk powder and 0.1% Tween-20 and all at 45° C. The slides were allowed to air dry in the dark, and then 10 ul of propidium iodide counterstain (Imagenetics) and a coverslip, added to each.

Digoxigenin-Labelled Y-Chromosome Probe [Boehringer Mannheim]

Each slide received 20 ul of the hybridisation mixture, consisting of: 10 ul formamide [50% of final volume]; 5 ul 4× hybridisation solution; 2.5 ul probe [50 ng]; 2.5 ul 8× blocking solutions. The mixture was covered by a silanised glass coverslip, sealed and then denatured for 5->10 mins at 72° C. on a prewarmed glass plate in the oven, before incubation in a moist chamber at 37° C. overnight. The slides were washed for 3×5 mins in 2×SSC, prior to 30 mins in 50 ml TBS containing 1× blocking solution (as above) and 1% Boehringer kit blocker reagent—both also at 37° C. To promote detection, the slides were transferred to 50 ml TBS and 50 ul anti-digoxigenin alkaline phosphatase conjugate [200 ug/ml] containing 1% kit blocker reagent for 30 mins at 37° C., and then they were washed for 3×10 mins in 0.2% Tween 20 in TBS at room temperature. Immediately before use, 4.5 ul of NBT, 3.5 ul of X-phosphate and 0.24 mg of levamisole (Sigma) was added to 1 ml of Tris/NaCl/MgCl2 buffer. Appropriate volumes for the number and size of the sections were added and the slides incubated at room temperature in a humidified box covered in foil until the dark blue/purple colour developed. To stop the reaction, the slides were rinsed for 5 mins at room temperature in 10 mM Tris-Cl/1 mM Na2 EDTA, pH 8.0.

Sections to be counter stained with propidium iodide were incubated for 5 mins at room temperature in the dark in 50 ml TBS+5 ul propidium iodide [1 mg/ml], or a similar concentration of acriflavine yellow, washed for 2-3 mins under running water, and then allowed to air dry in the dark. Finally, the sections were mounted in 20 ul of anti-fading solution under a glass coverslip, which was sealed at the edges with nail varnish.

Wound Contraction and Wound Closure Experiments

Collagen Gel Contraction Experiments

Specific populations of adult human cells were isolated by precise microdissection of the appropriate tissues (wastage from prior operations on 25-45 year old male and female donors), which were then used to initiate cell cultures by explant outgrowth. A similar approach was also employed to establish the different ages of rodent cells (as detailed below). Primary cultures (human and rat) were subpassaged about 2 to 3 weeks after their initiation, and all of the experiments were performed with either second or third passage cells some 2 to 4 weeks subsequently.

Type 1 collagen solution was prepared from adult rat tail tendons (20, 21). In brief, 1 g of U.V./ethanol-sterilised tail tendon was stirred in 300 ml of sterile 0.5M acetic acid for 48 hours at 4° C. The resulting solution was then filtered through several layers of sterile gauze, centrifuged at 2500 g for 3 hours, and dialysed for 24 hours against distilled water before undergoing further centrifugation. The collagen gel (which sets at 37° C.) was prepared by mixing the collagen solution with one tenth of it's volume of 10× concentrated MEM and approximately half of this volume of 4.4% $NaHCO_3$ to give a final pH of 7.3. Each population was seeded at the same density of $10^5$ cells per ml of collagen gel, 1.5 ml of which was placed into each 35 mm petri dish at 37° C. (95% air/5% $CO_2$) to set and then covered with about 0.5 ml of MEM (considered to be time=0). The diameter of 20-24 separate collagen gels were recorded for each cell type, every 4-6 hours for a period of 5 days. Further medium was added in small increments as the gels shrank.

We conducted further experiments to investigate the "knitting together" of cut edges of skin. Standardised cuts were made in small oblong pieces of human skin, either vertically across three quarters of their length, or horizontally right through them, just below the epidermis. The cut surfaces were then pressed back together with either skin fibroblasts, dermal papilla, dermal sheath or smooth muscle cells (that had been amassed into "tacky" lumps of viable cells with a rubber scraper) and subsequently sandwiched between. Very confluent petri dishes of cells were far superior sources to those that were low in numbers, since they produced stickier accumulations of cells. All of the pieces of skin were cultured in a non-liquid environment, that is on a permanently damp surface in a humid atmosphere 37° C., but never floating on, or submerged in, medium.

Storage of Dermal Sheath Tissue

Cold temperature storage of dermal sheath tissue/cells; additionally their subjection to adverse conditions to highlight stem cell-type characteristics—Including capacity for preferential survival.

Human skin samples (as detailed directly above) were cleaned and appropriately microdissected to provide: (a) 3 $mm^2$ portions of whole skin; (b) isolated hair follicles; (c) fragments of glassy membrane sandwiched between thin layers of sheath dermis and ORS epidermis, and (d) primary cultures of dermal sheath cells (prepared as above). Each of these four levels of tissue complexity were then subjected to six different forms of adverse conditions (each repeated with and without serum, and/or, glucose and glycerol): (i) prolonged cold temperature storage at 4° C.; (ii) repeated freeze/thaw cycles at −20° C.; (iii) repeated freeze/thaw storage at −80° C. in DMSO;

RESULTS

Sheath Implants

All of the sites that had been implanted with dermal sheath tissue healed rapidly and in a manner that seemed typical of any superficial skin lesion. Fine narrow scabs formed as the site dried and then were lost over the next few days to leave a very faint wound, which was almost imperceivable by about the 10th day. There was no external sign of any inflammatory reaction in or around the wounds, nor any physical perception of the site. The tip of a fibre that was darker and disproportionately sturdier for its length than any of the arm skins local vellus hairs, was first noticed on the 24th day after the dermal sheath had been introduced. On the 33rd day post-implantation, a second much finer and unpigmented fibre was seen to have emerged just to the side of the first. A very light peppering of pigmented material was also visible below the surface of the skin, in the immediate vicinity of the healed sites. In addition, a dark line of material could be seen underneath the skin-directly behind the base of the larger fibre (refer to FIGS. 4 and 5). This almost certainly represented a continuation of the exposed length of hair, and indicated that the follicle producing it was shallowly embedded and at an unusual angle and orientation relative to the local follicles. Both fibres increased in mass and length over the next few weeks, but this was more pronounced in the pigmented fibre which became more obviously stouter and thus morphologically distinct from the local hairs (refer to FIGS. 4 and 5). The finer white fibre was covered by a thin layer (or sac) of dried cells, but otherwise, was quite similar in stature and general appearance to the neighbouring non-induced hairs. Twenty one days after the second set of operations (initiated three months after the first) a fibre (again darker and sturdier than the local hairs) was seen at the sheath-implanted site. Over a further similar time span of three weeks, this solidly pigmented hair grew thicker and became more curved. The site was biopsied on day 42.

Figure 6:
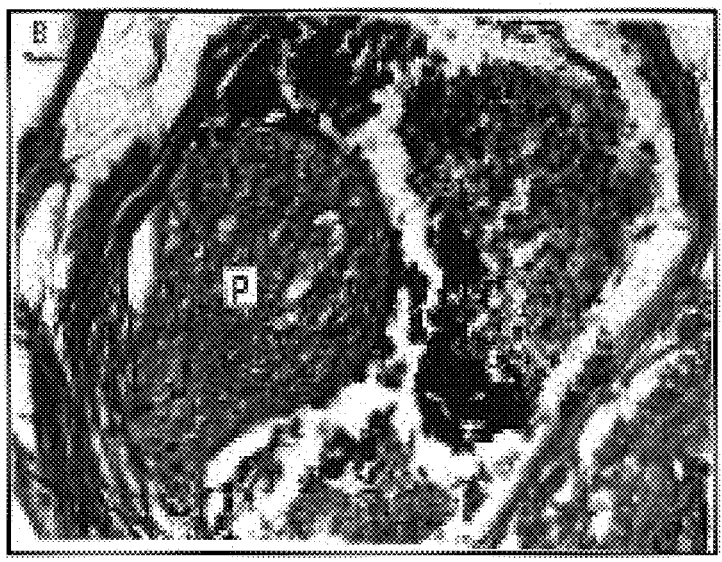
FIG. 6 represents pictorial evidence of a histological section through an end bulb region of an induced follicle, revealing an Alcian blue-positive stained papilla (P).

Histological examination of the sheath-implanted sites confirmed that the two larger follicles which had produced terminal-type fibres externally, had all of the characteristic components. For instance, large oval (Alcian blue-positive) dermal papillae (FIG. 6, legend P) were overlaid by a pigmented epidermal matrix, and follicle-typical concentric tissue layers could also be clearly seen in transverse sections. However, these follicles were quite different from the local vellus population in terms of their: larger size; shallow depth of growth within the skin, and unusual angle of orientation parallel to the skin surface. Such independent and contrasting features strongly suggest that the larger appendages were induced.

Notably, none of the transplanted material was transplanted into an immunoprotected site.

Further smaller follicles were also noted in random positions and arrangements in and around the post-experimental wound sites, and while they too may have been newly formed, their situation could not be interpreted on the basis of the morphological criteria alone.

Evidence in Support of Immunoprivilege as Illustrated by In Situ Hybridisation

Both positive (refer to FIG. 7 which represents pictorial evidence of a lower portion of an induced follicle which can be seen to stain positively following in-situ hybridisation with a Y-chromosome-specific DNA probe, realised via digoxygenin label) and negative (refer to FIG. 8 which represents pictorial evidence of a tissue section acting as a negative control for FIG. 7, and represents female skin that is not stained at all by the digoxygenin-linked Y-chromosome probe) controls stained appropriately to confirm the validity of the protocols basic methodology.

Figure 7:
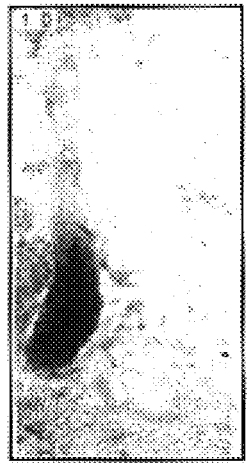
FIG. 7 represents pictorial evidence of a lower portion of an induced follicle which can be seen to stain positively following in situ hybridisation with a Y-chromosome-specific DNA probe, realised via digoxygenin label.
Figure 8:
FIG. 8 represents pictorial evidence of a tissue section acting as negative control for FIG. 7 and represents female skin that is not stained at all by the digoxygenin-linked Y-chromosome probe.
Figure 9:
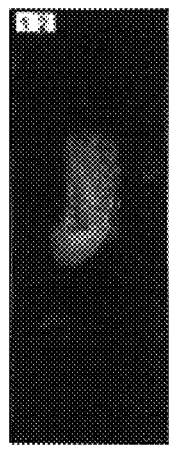
FIG. 9 represents pictorial evidence of a lower portion of an induced follicle stained positively following in situ hybridisation with a Y-chromosome-specific DNA probe, realised via a green fluorophore marker.
Figure 10:
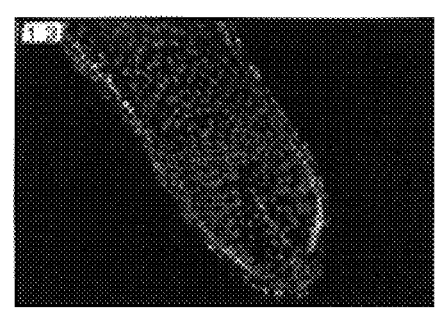
FIG. 10 represents pictorial evidence of a tissue section acting as a positive control for FIG. 9.

In the first set of experimental tissue sections, both of the Y-chromosome-specific DNA probes recognised some of the smaller follicles in the wound sites, as well as the more predictably induced larger ones. Only the lowermost regions of the smaller follicles, in fact, little more than the end bulb regions, repeatedly stained positively with the probes (compare FIGS. 7 and 8), as visualised by either the digoxygenin or the Spectrum green fluorophore to indicate the cells of male origin. Unfortunately, the morphological resolution of the tissue was not adequate to interpret the probes distribution at the level of individual cells, or even tissue layers. Nevertheless, that both the fluorophore, (refer to FIG. 9 compared to FIG. 10) and digoxygenin—(FIG. 7 compared to 8) labelled probe recognised almost identical regions of the follicles tissue as positive, was considered to reinforce the results.

Experimental Evidence in Support of the Ability of Dermal Sheath Cells to Provide Long Term Replacement Skin Dermis Dermal sheath cells were recombined with epidermal cells from hair follicles and grafted, inside a chamber that separated the graft from the surrounding skin cells, onto an animal.

Figure 11:
FIG. 11 represents pictorial evidence of a high power magnification view of the side of a long term [24 days] graft.
Figure 12A:
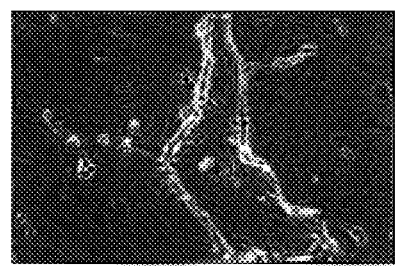
Figure 12B:
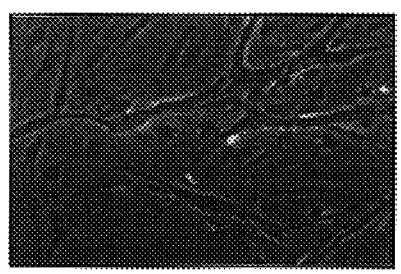
Figure 12C:
Figure 12D:
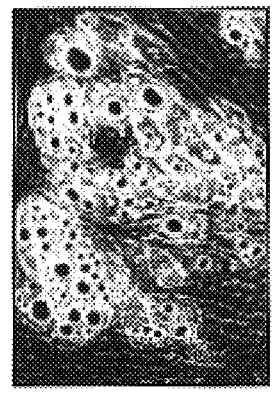
Figure 12E:
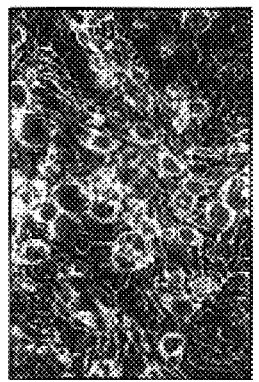
Figure 12F:
Figure 12G:
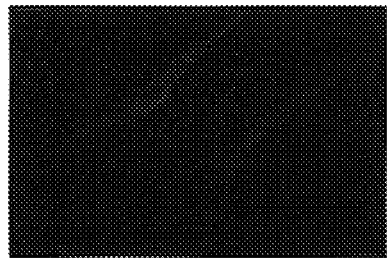
Figure 12H:
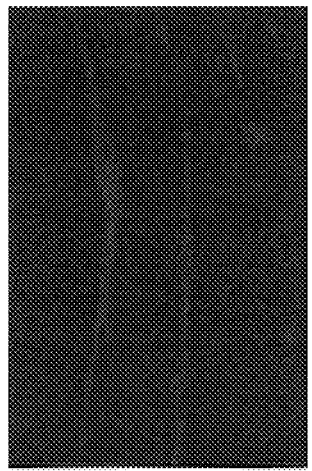
Figure 12I:
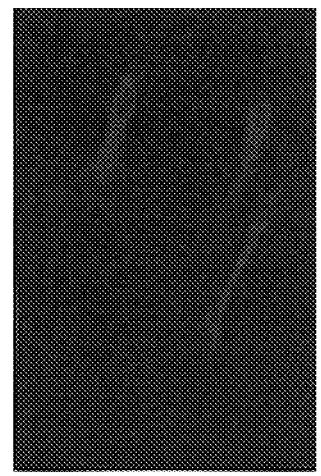

The dermal sheath cells formed a very good dermis with uniform cell density and no sign of abnormal collagen formation. They also interacted with the epidermis to produce a thick epidermal covering. A complete and normal basement membrane was formed between dermal sheath and epidermis. Where the chamber surrounding the graft has been removed, the white block cell infiltrate that has built up outside the graft does not appear to enter the new skin site. Refer to FIG. 11 which represents a high power magnification view of the side of a long term [24 days] graft. The line of dark dense white blood cell infiltrate on the left, has not encroached into the graft site. In the dermis, collagen bundles are structured, dermal cells are regularly distributed and a complete and normal basement membrane is obvious.

Experimental Evidence in Support of Dermal Sheath Cell Stem Cell Potential

FIG. 12 (A-I) represent pictorial evidence of dermal sheath cells capability to differentiate into different mesenchymal cells and hence their stem cell potential. It can be seen that these cells can differentiate into myotubes, adipocytes, chondrocytes and mineral producing bone cells. Further surprising evidence includes hair follicle tissue, obtained from individuals in the 95-105 age range, was found to be viable and capable of acting as a productive source for cell culture initiation. This data supports the hypothesis of the capability of stem cells to differentiate and reproduce remains constant during lifetime (22). Additionally repeated freezing and thawing of primary dermal sheath cells and subsequent cloning did not alter their potential to exhibit at least four different phenotypes despite their prior exposure to adverse conditions.

Experimental Evidence in Support of Follicle Dermal Sheath Lineage Potential

Muscle Myotubes

Subpopulations of small spindle-shaped cells were observed both singularly and in various states of fusion (as can also be commonly seen in routinely prepared cultures), some forming long branching, multinucleate myotube-like structures.

A proportion of these cells strained positively with myosin, desmin and/or alpha-smooth muscle actin monoclonal antibodies. [There have even been an odd occasion in the past when we have observed spontaneous rhythmic beating, i.e. contractions, of long aggregations of such muscle precursor-type cells in our petri dishes].

Adipocytes

These cells were identified by their distinctive multivesiculate appearance and the fact that the material contained within their vesicles was stained red by Sudan IV, and thus shown to be saturated neutral lipid.

Chondrocytes

Seen as accumulations of rounded cells with pericellular pH 1.0 Alcian Blue positive material which would be chondriotin and keratan sulphate proteoglycans, and lacunae between many of the cells—{interestingly similar cell behaviour is observed when rat dermal sheath cells are mixed with microdissected ear cartlidge in vitro}. This also seems likely to be related to our observations in vivo, when implanted dermal sheath cells appear to simulate hyperplasia in the normally inactive ear cartilage.

Mineral Producing Bone Cells

These cells were identified by their formation of aggregates in which the matrix appeared mineralised and stained positively for calcium phosphates, after being treated by the von Kossa method.

Further distinctive cell types have also been observed in our dermal sheath cell cultures (including interesting dendritic populations) but as yet these remain inaccurately defined.

Experimental Evidence in Support of Dermal Sheath Cells as Substitutes for Fibroblasts in Skin Wounding Fluorescent dye (DiI) labelled dermal sheath cells and fibroblasts were implanted into skin wounds in a collagen gel, dermal sheath cells survived comparably to skin cells over 10 days and were observed to penetrate further into host skin. Dermal sheath cells were also shown to be capable of migration and incorporating themselves into normal skin away from the wound itself (refer to FIG. 13 which represents pictorial evidence of skin at the margin of a wound and in which dermal sheath cells have surrounded an isolated follicle remote in undamaged tissue).

Evidence in Support of Wound Contracture

Wound contracture is a very important part of the process by which skin heals, and it is thought that a transient population of cells called myofibroblasts, effect this closing of the damaged site by contraction. The exact source of the myofibroblasts has until now, not been identified, but they are characterised by their expression of alpha-smooth muscle actin.

We conducted studies which compared the abilities of follicular and non-follicular dermal cells from three different ages of rat, and from different skin sites in adult humans, to contract collagen gel lattices. The adult human cell types involved were derived from skin fibroblasts from four different body sites; specifically smooth muscle cells; scalp follicle dermal papilla and, lower, mid and upper follicle dermal sheath cells. The rodent cells were derived from newborn, 14 day, and adult animals skin fibroblasts from four different body sites, [ear, mystacial, dorsal, footpad]; aortic smooth muscle cells, and vibrissa follicle dermal papilla and sheath cells.

Results showed that all of the follicle-derived dermal cell types were able to contract gels to a much greater extent than (roughly double) either the smooth muscle cells, or any of the body regions of skin fibroblasts. The contractile capabilities of the adult rat vibrissa-derived dermal cells, was similar to that of the newborn rat skin fibroblasts and smooth muscle cells. Although, in any one age group, the follicle-derived cells were always more contractile than either skin fibroblasts or smooth muscle cells (which behaved quite similarly).

Of the four cell types investigated, the dermal sheath cells were by far the most able promoters of the "knitting together" process. They alone formed stable joins between two damaged edges of skin portion, whether the cut had been made vertically, or horizontally. Occasionally, they appeared to have actually sealed the cut surfaces together, since no gaps were evident externally as the overlying epidermis was continuous. The dermal papilla cells, while a lot less effective than the dermal sheath (perhaps a third as good), were better than controls of no cells at all. The smooth muscle cells capabilities to effect reassociation of the tissue seemed on a par with not having introduced any cells into the wounds, but the skin fibroblasts actually appeared to hinder any "sticking" at all.

Although conducted in vitro, this work supports the proposition that follicle-derived dermal cells may promote wound healing processes in vivo.

Storage of Dermal Sheath Tissue

Our investigations have shown that dermal sheath tissue and/or cells derived therefrom can be stored long term at low temperatures and yet still, when subjected to appropriate conditions, grow. This clearly has important implications in the storage of wound healing therapeutics, and specifically, the storage of grafts or "living skins" made therefrom.

Moreover, our investigations have also shown that the dermal sheath cells can persist for a long time in culture under extreme stress. This is also of important implications for wound healing therapeutics derived from this tissue type and tends to simply that the tissue type is suitably robust, and displays stem cell characteristic durability and viability.

In short, not only does dermal sheath tissue and/or cells derived therefrom have all the advantageous properties that one might hope to find in a wound healing tissue type but it also has properties that facilitate the use of the tissue in terms of manufacturing and long term storage.

REFERENCES

1. Malkinson, F. D. and Kean, J. T. (1978). Hair matrix cell kinetics: a selective review. Int J Dermatol. 17, 536-551.
2. Oliver, R. F. (1971). The dermal papilla and the development and growth of hair. J. Soc. Cosmet. Chem. 22, 741-755.
3. Oliver, R. F. and Jahoda, C. A. B. (1989). The dermal papilla and maintenance of hair growth. In the biology of wool and hair. (ed. G. E. Rogers, P. J. Reis, K. A. Ward and R. C. Marshall), pp.51-67. Cambridge: Cambridge University Press.
4. Reynolds, A. J. and Jahoda, C. A. B. (1992). Cultured dermal papilla cells induce follicle formation and hair growth by transdifferentiation of an adult epidermis. Development 115, 587-593.

5. Reynolds, A. J., Lawrence, C. and Jahoda, C. A. B. (1993). Culture of human hair follicle germinative epidermal cells. J. Invest. Dermatol. 101, 634-638.
6. Oliver R. F., (1980). Local interactions in mammalian hair growth. In the skin of vertebrates (Ed. Spearman R I C, Riley Pa.) New York: Academic Press, 199-210.
7. Reynolds, A. J. and Jahoda, C. A. B. (1991a). Inductive properties of hair follicle cells. In the Molecular and Structural Biology of Hair. Proc. N.Y. Acad. Sci. 624, 226-242.
8. Jahoda, C. A. B. (1992). Induction of follicle formation and hair growth by vibrissa dermal papillae implanted into rat ear wounds: vibrissa-type fibres are specified. Development 115, 1103-1109.
9. Jahoda, C. A. B., Reynolds, A. J. and Oliver, R. F. (1993). Induction of hair growth in ear wounds by cultured dermal papilla cells. J. Invest. Dermatol. 101, 584-590.
10. Weinberg, W. C., Goodman, L. V., George, C., Morgan, D. L., Ledbetter, S. and Yuspa, S. H. (1993). Reconstitution of hair follicle development in vivo: determination of follicle formation, hair growth, and hair quality by dermal cells. J. Invest. Dermatol. 100, 229-236.
11. Lichti, U., Weinberg, W. C., Goodman, L., Ledbetter, S., Dooley, T., Morgan, D. and Yuspa, S. H. (1993). In vivo regulation of murine hair growth: insights from grafting defined cell populations onto nude mice. J Invest Dermatol. 101, 124s-129s.
12. Watson, S. A. J., Pisansarakit, P. and Moore, G. P. M. (1994). Sheep vibrissa dermal papillae induce hair follicle formation in heterotypic skin equivalents. Br. J. Dermatol. 131, 827-835.
13. Hage J. J., and Bouman F. G. (1991). Surgical depilation for the treatment of pseudofoliculitis or local hirsutism of the face: experience in the first 40 patients. Plast Reconstr Surg 1991; 88, 446-51.
14. Inaba, M. & Inaba, Y. (1992). Chapter 16. The Question of Hair Regeneration. In: Human Body Odor, Etiology, Treatment and Related Factors. Springer-Verlag, Tokyo (printed in Hong Kong). Pp. 235-260.
15. Jahoda, C. A. B., Oliver, R. F., Reynolds, A. J., Forrester, J. C. and Horne, K. A. (1996). Human hair follicle regeneration following amputation and grafting into the nude muouse. J Invest Dermatol. 107, 804-807.
16. Reynolds, A. J. and Jahoda, C. A. B. (1993). Hair fibre progenitor cells: developmental status and interactive potential. Pp.241-250. In Serminars in Developmental Biology, Vol. 4.
17. Scott D. M., Ehrmann I. E., Ellis P. S., et al. Identification of a mouse male-specific transplantation antigen, H-Y. Nature 1995; 376: 695-8.
18. Kemp, C. B. et al., (1973). Diabetologia 9: 486-491.
19. Yagita H, Seino K-I, Kayagaki N, Okumura K. (1996). CD95 ligan in graft rejection. Nature 379: 682-3.
20. Elsdale, T. & Bard, J. (1972). Cellular interactions in mass cultures of human diploid fibroblasts. Nature 236: 152-153.
21. Michalopoulos, G & Pitot, H. C. (1975). Primary culture of parenchymal liver cells on collagen membranes. Morphological and biochemical observationss. Exp. Cell Res. 94: 70-78.
22. Haynesworth, S. E., Goldberg, V. M. & Caplan, A. I. (1993). Diminution of the number of mesenchymal stem cells as a cause for skeletal aging. Chapter 7. In: Musculoskeletal soft-tissue ageing impact on mobility. (Eds. J. A. Buckwater & V. M. Goldberg). Pp. 79.87.

The invention claimed is:

1. A method for healing a skin wound by promoting the formation and growth of dermis tissue, comprising applying to a subject in need thereof a composition consisting of isolated dermal sheath cells, said method comprising:
   (a) obtaining isolated dermal sheath cells capable of differentiating into mesenchymal cells and providing dermal-epidermal recombination; and
   (b) applying the dermal sheath cells of step (a) to dermis of the skin wound;
   such that the dermal sheath cells form basement membrane and differentiated dermis, thereby healing the wound.

2. The method of claim 1 wherein the cells of step (a) are capable of differentiating into myotubes, adipocytes, chondrocytes, and mineral-producing bone cells.

3. The method of claim 1 wherein the dermal sheath cells provide a dermal wound bed.

4. The method of claim 1, wherein said isolated dermal sheath cells applied to the skin wound in step (b) are cultured dermal sheath cells.

5. A method for healing a skin wound by promoting the formation and growth of dermis tissue, comprising applying to a subject in need thereof a composition consisting of isolated dermal sheath tissue, wherein said composition is applied to dermis exposed by the skin wound of said subject, wherein said isolated dermal sheath tissue differentiates to form said dermis tissue.

6. The method of claim 5 wherein the isolated dermal sheath tissue consists of isolated dermal sheath cells.

7. The method of claim 5, wherein said dermis tissue consists of isolated dermal sheath cells, collagen bundles and basement membranes.

8. A method for healing a skin wound by promoting the formation and growth of dermis tissue, comprising applying to a subject in need thereof a composition consisting of isolated dermal sheath tissue embedded in a matrix material, wherein said composition is applied to dermis exposed by the skin wound of said subject, and wherein said isolated dermal sheath tissue embedded in a matrix material differentiates to form said dermis tissue.

9. A method for healing a skin wound, wherein said healing of a skin wound promotes formation and growth of dermis tissue, comprising applying a composition consisting of isolated dermal sheath cells to dermis exposed by the skin wound thereby promoting formation and growth of said dermis tissue.

10. A method for healing a skin wound by promoting the formation and growth of dermis tissue, comprising applying to a subject in need thereof a composition consisting of isolated dermal sheath tissue, wherein said composition is applied to dermis exposed by the skin wound of said subject, wherein the isolated dermal sheath tissue is capable of differentiating to form said dermis tissue.

11. A method for healing a skin wound of the dermis by promoting the formation and growth of dermis tissue, comprising:
   (a) isolating and separating dermal sheath cells from surrounding hair follicle cells to generate a population consisting of isolated dermal sheath cells;
   (b) preparing a composition consisting of said isolated dermal sheath cells; and
   (c) applying the composition of isolated dermal sheath cells to the dermis of the skin wound to promote formation and growth of dermis tissue to heal the skin wound.

12. The method of claim 11, wherein the population of isolated dermal sheath cells is further selected for cells expressing smooth muscle actin.

13. A method for promoting the formation and growth of basement membrane of dermis tissue in a skin wound, comprising applying to a subject having the skin wound a composition consisting essentially of isolated dermal sheath tissue, wherein said composition is applied to dermis exposed by the skin wound, wherein said isolated dermal sheath tissue is capable of promoting the formation and growth of basement membrane of dermis tissue.

* * * * *